Nov. 6, 1973
W. P. THOMSON
Plant Pat. 3,406
CARNATION PLANT
Filed Jan. 24, 1972
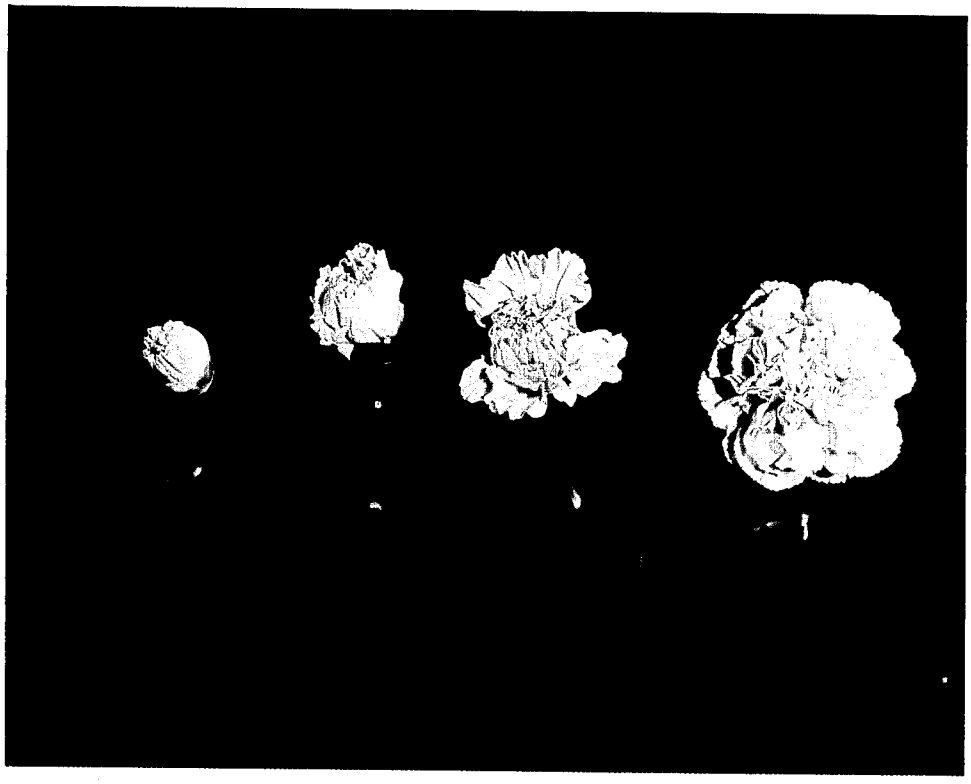
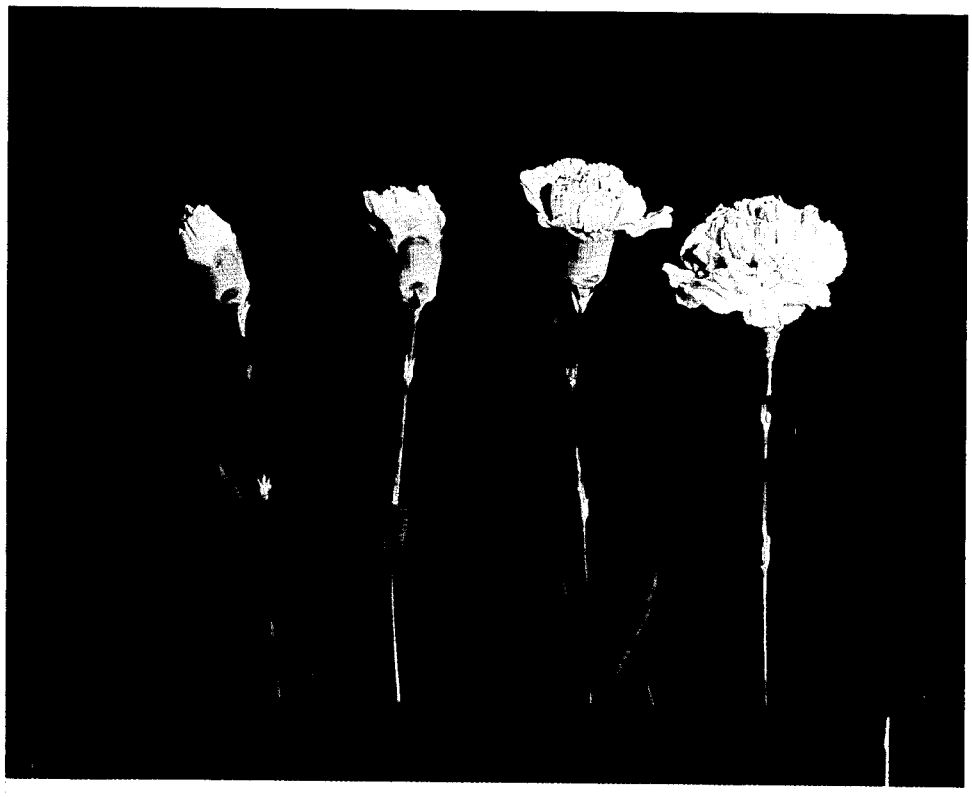

United States Patent Office

Plant Pat. 3,406
Patented Nov. 6, 1973

3,406

CARNATION PLANT

William Pomeroy Thomson, 74 Westland Ave., West Hartford, Conn. 06107

Filed Jan. 24, 1972, Ser. No. 220,501
**Int. Cl. A01h *5/00***
U.S. Cl. Plt.—71 1 Claim

ABSTRACT OF THE DISCLOSURE

A new variety of carnation plant discovered in the course of meristem culture of the unpatented variety Barlo, which is of French origin, the new variety being a sport of Barlo and being especially distinguished by its remarkable resistance to splitting.

BACKGROUND OF THE NEW PLANT

This new carnation variety originated as a meristem of the unpatented variety Barlo and was cultured by me at West Hartford, Conn., in March of 1969. The new variety is a sport of Barlo which was a sport of Lolita (unpatented) which, in turn, originated as a sport of Ember Sim (unpatented). My propagation of the new variety, by cuttings and under glass, at West Hartford, Conn., led to the discovery that although the new variety closely resembled its parent in many respects, it is remarkably free of splitting.

This discovery has now resulted in commercial scale propagation, by cuttings, at West Hartford, Conn., and such continued propagation has demonstrated that while the parent Barlo, grown under glass, sustained a loss of about 15% by splitting, the greenhouse grown plants of the new variety suffered a splitting loss of less than 1%. Successive generations of this new variety asexually propagated at West Hartford, Conn., under my direction, have conclusively demonstrated that the characteristic of being practically free from splitting is firmly fixed and runs true from generation to generation.

DESCRIPTION OF THE DRAWINGS

This new variety of carnation plant is illustrated by the accompanying drawings which show the color characteristics of the flower as nearly true as it is reasonably possible to obtain through conventional photographic procedures. The upper view shows the flower development from the bud, at first opening, to the fully opened bloom as seen from a quarter angle above the specimens; and the lower view shows the same specimens as seen from a lower quarter angle to show the stems, leaves and calyx.

DESCRIPTION OF THE NEW PLANT

The following is a detailed description of my new variety of carnation plant with color designations according to the Methuen Handbook of Colour, second edition, published in 1967 by Methuen & Co. Ltd. of London, England.

*The plant*

Origin: Sport.
Parentage: Barlo (unpatented).
Classification:
- *Bontanic.*—Dianthus Caryophyllus.
- *Commercial.*—Carnation.

Form: Bush.
Height: Normally a few inches shorter than most Sim varieties.
Growth: Vigorous and branching, with strong upright stems when supported.
Foliage: Quantity—normal for Sim varieties usually with 14 to 18 pairs of leaves per stem.

- *Leaf size.*—4 to 5 inches long and approximately ½ inch wide.
- *Shape.*—Curly with long-acuminate tip and entire margin.
- *Texture.*—Smooth.
- *Color.*—Both upper side and under side are of the same Green.
- *Ribs.*—A single rib along the center of the leaf.
- *Petioles.*—None. The leaf is decurrent and amplexicaul.

*The bud*

Form: Ovoid.
Size: 1 to 1¼ inch tall and ¾ to 1 inch in diameter just before opening.
Opening Rate: Normal for Sim variety.
Color:
- *When sepals first divide.*—Pale Pink 10A3.
- *When petals begin to unfurl.*—Pale Pink 10A3 to 10A4.

Sepals: Spear shaped and stand up from the calyx.
- *Color.*—Light Green.

Calyx:
- *Shape.*—Cupped and broad with five upright segments.
- *Size.*—Large.
- *Aspect.*—Smooth.
- *Splitting.*—Very seldom.

*The flower*

Blooming Characteristics: Profusely and continuously all year long.
Size of Bloom: Medium. 3 to 3½ inches in diameter and 1¼ to 1½ inches in depth.
Borne: Singly—after disbudding.
Shape: Generally round with a high center and flat outer petals. The blooms get slightly larger as flower ages.
Petalage: 60 to 70 petals.
- *Form.*—Symmetrically round with smooth margin.
- *Color.*—Both inside and outside petals have a soft Light Pink top side color between 10A3 and 10A4 which is uniform to the base where the color turns to a Light Green. The reverse side of the petals has a slightly lighter shade of soft Pink and closely matches 10A3.
- *Appearance.*—Satiny.

Peduncle: Sturdy, upright, ¼ inch to 1 inch long and of Green color.
Discoloration. Fades very slightly with age.
Effect of weather: Hot weather makes flowers smaller.
Fragrance: Slight.
Persistence: Flower hangs on and withers.
Lasting quality. Normal for Sim varieties. Approximately 7 to 10 days on plant and from 6 to 12 days as a cut flower.

*Reproductive organs*

Stamens:
- *Anthers.*—Arrangement — upright around ovary; length—½ to 1 inch; number—10 to 12.
- *Filaments.*—Length—approximately ⅛ inch; color—Pale Pink.
- *Pollen.*—Yellow in color.

Pistils: 2 in number; length—1¼ inch to 1½ inch. Color—Pink.
Stigmas: Color—Pale Pink.
Ovary: Slightly flattened pear-shaped, ¼ inch x ⅜ inch wide at base and ½ inch high with pointed top. Color—Light Green.
Fruit: Pear-shaped, fertile, and of Brown color at maturity.

This new variety of carnation plant most nearly resembles its parent Barlo and has almost the same color. A particular distinction, however, resides in the fact that this new variety experiences less than 1% loss from splitting when greenhouse grown as compared to a splitting loss of at least 15% for the parent variety Barlo. Other differences of this new variety when compared with its parent will be found in the color of the new variety being a shade deeper pink and the flowers are slightly smaller but formed more symmetrically round. Also, the new variety grows a few inches shorter than its parent and its leaves are slightly narrower than those of the parent.

I claim:

1. A new and distinct variety of carnation plant, substantially as herein shown and described, characterized in particular by its very low splitting habit and the more symmetrically round form and unique color of its blossoms when compared with its parent.

No references cited.

ROBERT E. BAGWILL, Primary Examiner